US011602323B2

(12) United States Patent
Chaudhury et al.

(10) Patent No.: US 11,602,323 B2
(45) Date of Patent: Mar. 14, 2023

(54) COMPUTED TOMOGRAPHY DEVICE AND METHOD FOR OPERATING A COMPUTED TOMOGRAPHY DEVICE (71) Applicant: Siemens Healthcare GmbH, Erlangen (DE)

(72) Inventors: Shameem Kabir Chaudhury, Erlangen (DE); Thomas Hilderscheid, Altdorf (DE); Thomas Hofmann, Grossenseebach (DE); Bjoern Kreisler, Hausen (DE); Christian Schroeter, Bamberg (DE); Stefan Woelfel, Dormitz (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 155 days.

(21) Appl. No.: 17/019,723

(22) Filed: Sep. 14, 2020

(65) Prior Publication Data
US 2021/0085278 A1 Mar. 25, 2021

(30) Foreign Application Priority Data

Sep. 20, 2019 (EP) .................................... 19198590

(51) Int. Cl.
A61B 6/00 (2006.01)
G01T 1/175 (2006.01)
G01T 1/24 (2006.01)

(52) U.S. Cl.
CPC ............. *A61B 6/56* (2013.01); *A61B 6/4208* (2013.01); *G01T 1/175* (2013.01); *G01T 1/24* (2013.01)

(58) Field of Classification Search
None
See application file for complete search history.

(56) References Cited

U.S. PATENT DOCUMENTS

| 9,636,078 B2 | 5/2017 | Ergler et al. |
| 10,348,125 B2 * | 7/2019 | Carnemark ............. H02J 3/381 |
| 2012/0033783 A1 | 2/2012 | Katayama |
| 2013/0048869 A1 | 2/2013 | Kominami et al. |
| 2015/0182183 A1 * | 7/2015 | Ergler .................... A61B 6/035 378/91 |

FOREIGN PATENT DOCUMENTS

DE 102013227214 A1 7/2015

* cited by examiner

*Primary Examiner* — Edwin C Gunberg
(74) *Attorney, Agent, or Firm* — Harness, Dickey & Pierce, P.L.C.

(57) ABSTRACT

A computed tomography device includes a holding frame and a ring mount, being movably mounted to the holding frame. The ring mount includes an x-ray detector, with a semiconductor material, operable in an equilibrium of statistical states of occupation. In an embodiment, the computed tomography device includes a first power supply, set up to supply power, in an operating state of the computed tomography device, to a first lot of components of the computed tomography device, the first lot of components being arranged on the ring mount for an image generation process; and a second power supply, separable from the first power supply in terms of circuitry, to supply power to a second lot of components of the computed tomography device in a resting state of the computed tomography device, the components of the second lot being set up to hold the semiconductor material in the equilibrium.

14 Claims, 1 Drawing Sheet

COMPUTED TOMOGRAPHY DEVICE AND METHOD FOR OPERATING A COMPUTED TOMOGRAPHY DEVICE

PRIORITY STATEMENT

The present application hereby claims priority under 35 U.S.C. § 119 to European patent application number EP 19198590.2 filed Sep. 20, 2019, the entire contents of which are hereby incorporated herein by reference.

FIELD

Embodiments of the invention generally relate to a computed tomography device (CT) with a holding frame and a ring mount, which is mounted movably with respect to the holding frame, wherein the ring mount has an x-ray detector with a semiconductor material, which is operable in an equilibrium of statistical states of occupation, and wherein the CT has a power supply which is set up, in one operating state of the CT, to supply power to a lot of components in the CT which are arranged on the ring mount for an image generation process. Embodiments of the invention also generally relate to a method for operating such a CT.

BACKGROUND

In a modern CT, a direct-conversion x-ray detector based, for instance, on cadmium telluride or cadmium zinc telluride (or comparable semiconductor materials with similarly relevant properties) is used in particular for photon-counting applications. After commissioning, a detector of this type has a counting rate drift which may result in artifacts during the imaging. For a reliable, high-resolution and interference-free image generation, it is necessary for the cadmium telluride or the cadmium zinc telluride to have achieved a stable state of equilibrium with respect to an occupation of impurities after the activation operation of the CT.

One such state of equilibrium of the occupation of impurities is dependent here on the voltage applied to the x-ray detector. The achievement of a state of equilibrium which is adequate for an artifact-free image generation after activating a high voltage on the x-ray detector is a process which can last over a period of several hours. For operation in day-to-day medical practice, it is desirable, for efficiency reasons, to have the CT available as continuously operational as possible. The length of time required to achieve the state of equilibrium, which, in the case of a daily activation operation in practical work, would result in significant losses of time for examinations, stands opposed to this.

SUMMARY

At least one embodiment of the invention specifies a CT which is able to transfer an x-ray detector with an operable semiconductor material in an equilibrium of statistical states of occupation as quickly and easily as possible into a state ready for operation. At least one embodiment of the invention further specifies a method for operating a CT.

At least one embodiment of the invention is directed to a CT comprising a holding frame and a ring mount, mounted movably with respect to the holding frame, wherein the ring mount has an x-ray detector with a semiconductor material, which is operable in an equilibrium of statistical states of occupation, and wherein the CT has a first power supply which is intended and set up, in one operating state of the CT, to supply power to a first lot of components in the CT which are arranged on the ring mount for an image generation process.

At least one embodiment of the invention is directed to a method for operating a CT, which includes a holding frame and a ring mount mounted movably with respect to the holding frame, wherein the ring mount has an x-ray detector with a semiconductor material, which is operable in an equilibrium of statistical states of occupation. In accordance with at least one embodiment of the method, provision is made in an operating state of the CT to supply power to a first lot of components arranged on the ring mount via a first power supply and for a medical imaging process to be carried out via components of the first lot and in a resting state of the CT to supply power to a second lot of components arranged on the ring mount via a second power supply which is separated from the first power supply in terms of circuitry, and for the semiconductor material to be held in the equilibrium via the components of the second lot.

In at least one embodiment, the second power supply comprises in particular a second transmission path, which is set up to transmit power for the second power supply from the holding frame to the ring mount. In this regard the second transmission path is preferably separable from a first transmission path in terms of circuitry, the first transmission path being set up to transmit power for the first power supply from the holding frame to the ring mount. In this regard the first transmission path and the second transmission path are arranged preferably spatially separated from one another in terms of their respective components at least on the ring mount and can be separated in terms of circuitry, by at least their electric circuits on the ring mount being able to be separated from one another via a corresponding switching element.

At least one embodiment of the invention is directed to a computed tomography device comprising:

a holding frame; and a ring mount, the ring mount being movably mounted to the holding frame, and the ring mount including an x-ray detector, with a semiconductor material, operable in an equilibrium of statistical states of occupation;

a first power supply, set up to supply power, in an operating state of the computed tomography device, to a first lot of components of the computed tomography device, the first lot of components being arranged on the ring mount for an image generation process; and a second power supply, separable from the first power supply in terms of circuitry, to supply power to a second lot of components of the computed tomography device in a resting state of the computed tomography device, the components of the second lot being set up to hold the semiconductor material in the equilibrium.

At least one embodiment of the invention is directed to a method for operating a computed tomography device including a holding frame and a ring mount, the ring mount being movably mounted with respect to the holding frame, the ring mount including an x-ray detector with a semiconductor material, operable in an equilibrium of statistical states of occupation, the method comprising:

supplying, in an operating state of the computed tomography device, a first lot of components arranged on the ring mount with power via a first power supply and carrying out a medical imaging process via components of the first lot; and supplying, in a resting state of the computed tomography device, a second lot of components arranged on the ring mount with power via a second power supply, the second power supply being separated from the first power supply in terms of circuitry and holding the semiconductor material in the equilibrium via the components of the second lot.

BRIEF DESCRIPTION OF THE DRAWINGS

An example embodiment of the invention is then explained in more detail on the basis of a FIGURE. The FIGURE shows schematically.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the FIGURES. It will be understood that the spatially relative terms are intended to encompass different orientations of the device in use or operation in addition to the orientation depicted in the FIGURES. For example, if the device in the FIGURES is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the FIGURES. For example, two FIGURES shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the FIGURE. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central At least one processor (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central At least one processor (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer at least one processors into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc.

Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention is directed to a CT comprising a holding frame and a ring mount, mounted movably with respect to the holding frame, wherein the ring mount has an x-ray detector with a semiconductor material, which is operable in an equilibrium of statistical states of occupation, and wherein the CT has a first power supply which is intended and set up, in one operating state of the CT, to supply power to a first lot of components in the CT which are arranged on the ring mount for an image generation process.

At least one embodiment of the invention is directed to a CT having a second power supply which can be separated from the first power supply in terms of circuitry and which is intended and set up, in a resting state of the CT, to supply power to a second lot of components of the CT, wherein the components of the second lot are intended and set up to hold the semiconductor material in the equilibrium. Advantageous and in part separately considered inventive developments are the subject matter of the claims and of the description which follows.

At least one embodiment of the invention is directed to a method for operating a CT, which includes a holding frame and a ring mount mounted movably with respect to the holding frame, wherein the ring mount has an x-ray detector with a semiconductor material, which is operable in an equilibrium of statistical states of occupation. In accordance with at least one embodiment of the method, provision is made in an operating state of the CT to supply power to a first lot of components arranged on the ring mount via a first power supply and for a medical imaging process to be carried out via components of the first lot and in a resting state of the CT to supply power to a second lot of components arranged on the ring mount via a second power supply which is separated from the first power supply in terms of circuitry, and for the semiconductor material to be held in the equilibrium via the components of the second lot. At least one embodiment of the inventive method shares the advantages of the inventive CT. The advantages specified for the CT and for its developments can be analogously transferred to the method.

In this regard the semiconductor material of the x-ray detector is the material upon which an x-ray radiation strikes, which is emitted by an x-ray source of the CT for an examination of a human body part and in the process is in part absorbed and/or scattered hereby. This x-ray radiation striking the semiconductor material is converted by the same, inter alia by scattering processes such as the Compton effect and by the photoelectric effect, in particular into a current or voltage signal. In this regard the operability of the semiconductor material is understood to mean a state in which a recording procedure can be carried out with the CT with at least an adequate image quality and resolution for a medical imaging process.

In this regard an equilibrium of statistical states of occupation is understood inter alia to mean a defined distribution of impurities and/or charge carriers in the semiconductor material. In particular, this also includes such a state of equilibrium which has an electrodynamic equilibrium. Here the equilibrium of statistical states of occupation comprises in particular an equilibrium semiconductor material such that when x-ray radiation strikes the semiconductor material and free charge carriers are generated there as a result thereof, these are essentially movable unhindered in the semiconductor material if a voltage is applied to the semiconductor material. In particular, in the equilibrium, the x-ray radiation involves no change to an internal resistance in the semiconductor for the flux of the generated charge carriers specified by the bias voltage.

The state in which the first power supply is deactivated is in particular understood to mean the resting state of the CT. In the operating state, the first power supply supplies power in particular to the x-ray detector and a significant number of further loads on the CT. In particular, the first power supply is understood to mean the power supply which bears the main load of an electrical power supply of the load during a recording process and in the temporal environment of the same.

The first lot of components comprises in particular at least one x-ray source, e.g. an x-ray tube, which, if applicable, can have an anode motor for a rotary anode, cooling units and/or fans preferably for discharging thermal power generated in the x-ray source, and furthermore the x-ray detector, moreover electronic components connected hereto for signal resolution and image processing, for instance in the form of ASICs.

The second lot of components comprises components arranged in particular for the operation of the x-ray detector such as e.g. a voltage supply for generating a bias voltage in the semiconductor material for a separation of charge carriers generated by an incident x-ray radiation, a heating element for heating the semiconductor material and/or a light-emitting element for irradiating the semiconductor material, and if applicable a regulation device for regulating a temperature or an irradiation of the semiconductor material. The second lot of components.

In particular, individual components can be contained both in the first lot and also in the second lot if they are intended and set up both for an image generation and also for maintaining the equilibrium. In the operating state the second lot of components is supplied with power via the first power supply and in the resting state is supplied with power via the second power supply, wherein the other components of the first lot, which are not required immediately for the operability of the semiconductor material (and thus in particular not included in the second lot), are only supplied with power via the first power supply in the operating state, but do not receive power in the resting state.

The operability of the semiconductor material and thus of the x-ray detector presupposes an equilibrium of the statistical states of occupation, specifically the occupation of impurities by way of free charge carriers, in order to prevent the newly generated free charge carriers, which appear when x-ray radiation strikes the semiconductor material, from still occupying free impurities and thus not being available for counter events; this has a negative impact on the linearity.

To stop this, a bias voltage which effects a drift in the available free charge carriers in the semiconductor material is in particular applied on the one hand to the semiconductor material. Moreover, a "saturation" of the impurities in the semiconductor material is achieved by generating free charge carriers in the material by way of irradiation and moreover, if applicable, via heating, wherein the heating increases the mobility of the charge carriers in the semiconductor material.

Here the state of equilibrium only develops in an adequately stable manner after a few hours. For this purpose the cited components, which are required to achieve this equilibrium, must be supplied accordingly with power.

There may therefore be an inclination to consider continuous operation of the power supply of the x-ray detector.

The x-ray detector is arranged on the ring mount of the CT together with a plurality of other loads of the first lot of components. These loads represent, assuming an anode voltage of the x-ray tube, a continuously-operated basic load of a few kW. On account of this basic load, an uninterrupted operation of the ring mount, in other words even during the night and at weekends, would be energy-inefficient in terms of maintaining the state of equilibrium in the x-ray detector.

One possibility of avoiding this could be to configure the power supply of the load on the ring mount so that this has two switching or operating states, wherein during main operation all loads are supplied with power and during ancillary operation only the x-ray detector is supplied with power. A procedure of this type would however require a power distributor operating intelligently on the ring mount having to be designed to deactivate individual loads, and in this regard itself having to take over the distinction between the two operating states in control electronics set up specifically for this purpose, since all other electronic components in ancillary operation would be deactivated.

These control electronics must for their part be embedded in the communication of the other electronic components, wherein it would be taken into account that upon the transition from the ancillary operation into the main operation, the remaining components firstly run through their system start before they are completely communicable, in other words this could result in signal errors, while the control electronics of the power supply are already in operation. A solution of this type by way of a division of the power supply would therefore be prone to error which results in such a solution variant being rejected not least against the background of the high demand for a particularly stable operation in the medical field; this is also reflected in licensing procedures.

A consideration now underlying at least one embodiment of the invention is that the semiconductor material of the x-ray detector is the easiest to transfer in a state ready for operation, if the state of equilibrium is continuously maintained. This implies a continuous power supply to at least the x-ray detector, since the state of equilibrium can be maintained in particular by a bias voltage, which is applied to the semiconductor material, and/or by heating and/or irradiating the semiconductor material.

As a result of the complex interaction described between different electrical loads in a CT, which moreover communicate with one another in part for image generation and processing purposes, a division of the power supply into individual supply elements which can be activated and deactivated is not desirable since this in particular could have a negative effect on the shared time synchronization and thus the communication of image-processing electronic components.

In accordance with at least one embodiment of the invention, on the other hand, a second power supply is now proposed, which is primarily set up to keep the semiconductor material of the x-ray detector in the resting state of the first power supply in an operable state.

In at least one embodiment, the second power supply comprises in particular a second transmission path, which is set up to transmit power for the second power supply from the holding frame to the ring mount. In this regard the second transmission path is preferably separable from a first transmission path in terms of circuitry, the first transmission path being set up to transmit power for the first power supply from the holding frame to the ring mount. In this regard the first transmission path and the second transmission path are arranged preferably spatially separated from one another in terms of their respective components at least on the ring mount and can be separated in terms of circuitry, by at least their electric circuits on the ring mount being able to be separated from one another via a corresponding switching element.

The first transmission path here comprises in particular inductive elements, such as e.g. transmission coils, for inductive and in particular contactless power transmission from the holding frame to the ring mount, and/or a collector ring and corresponding collector contacts for the power transmission. The second transmission path preferably likewise comprises inductive elements of the described type and/or a terminal for a mains cable which is arranged on the ring mount. For the use of the terminal, the ring mount is preferably moved into a rest position, so that the terminal for the mains cable to be connected is accessible.

The CT preferably comprises an uninterruptible power supply (UPS), which can be interconnected with the second lot of components and particularly preferably with the second power supply. In this regard in the case of a power failure or in the case of brief fluctuations in power, such as may occur in the hospital environment as a result of significantly fluctuating loads, the UPS is intended and set up to supply power to the components of the second lot. This ensures that a power failure in the mains or power fluctuations do not result in a disruption to the equilibrium, which is to be maintained in the semiconductor material for its operability. In this regard the UPS can be arranged in particular on the holding frame and be interconnected at least in the case of use with the second power supply, so that the interconnection of the UPS with the components of the second lot can take place in particular by way of the second power supply.

The second lot of components favorably comprises a first voltage supply for applying a bias voltage to the semiconductor material. Here the first voltage supply has in particular switching elements for preparing the bias voltage from the power of the second power supply, connecting elements for connection to the semiconductor material and for applying the prepared bias voltage to this, and, if applicable, measuring and/or regulation elements for checking or regulating the bias voltage applied to the semiconductor material. The first voltage supply is preferably arranged on the ring mount and is moreover particularly preferably interconnected or interconnectable to the second power supply, in other words can be connected hereto by way of a switching element. The bias voltage provides for a corresponding drift of the free line carriers in the semiconductor material, so that there these occupy the impurities, as a result of which free charge carriers, which are generated by an x-ray radiation striking the semiconductor material, have a higher mobility in the semiconductor material, and in particular do not have the already saturated impurities there. This increases the linearity of the detector. Since it can take up to a few hours for the bias voltage to bring the semiconductor material into an equilibrium with respect to the occupation of impurities, it is therefore particularly advantageous to apply the bias voltage continuously to the semiconductor material via the first voltage supply.

The CT preferably comprises a third power supply which can be separated from the first power supply and the second power supply in terms of circuitry, the third power supply being interconnectable in particular with the first voltage supply and/or the second power supply, and which is intended and set up, with a system reboot of the CT, to supply power to the first voltage supply for maintaining the bias voltage on the semiconductor material during the system reboot. Here the third power supply comprises in particular a power buffer arranged on the ring mount, preferably in the form of a battery or a rechargeable battery, which can be fed and charged for instance in the operating state of the CT via the first power supply. The third power supply can however in particular also be implemented by an electric circuit which is within the second power supply and can be switched independently and can thus control in particular its second transmission path. In particular, the third power supply is set up to also maintain the bias voltage during maintenance work on other components in the second group if the second power supply is interrupted for the maintenance work.

For reasons of improved synchronization of the communication of different imaging and in particular signal-processing components, it is advantageous to carry out a system reboot of the CT at regular intervals, e.g. once a day. In this regard, the time synchronization of the individual components is in particular carried out again, which has a positive effect on the stability of the image generation and processing. With a system reboot of this type, the complete power supply of all components in the CT is usually interrupted. Via the third power supply configured as described, the first voltage supply can in particular also be supplied with power during the system reboot, so that the system reboot does not result in a voltage loss in the semiconductor material.

In an advantageous embodiment, the CT comprises a voltage buffer connected between the UPS and the first voltage supply, which is intended and set up to compensate for a voltage fluctuation when the UPS is in use. If the use of the UPS is required, for instance as a result of a power failure or as a result of considerable voltage fluctuations in the mains, voltage fluctuations may occur in the CT as a result of switching over to the power supply of the UPS. In order to compensate for this, a voltage buffer is connected upstream of the first voltage supply and compensates on the one hand for voltage and/or power fluctuations occurring due to the switchover process at an input of the first voltage supply and on the other hand bridges a possible runtime of the UPS until this is completely usable. In particular, the voltage buffer can also take the form of the power buffer of the third power supply.

The second lot of components favorably comprises a heating element for heating the semiconductor material and/or a light-emitting element for irradiating the semiconductor material. An irradiation of the semiconductor material via the light-emitting element is to be understood in this regard to mean that in addition to the x-ray source the CT has a light-emitting element which is set up to irradiate semiconductor material, while the x-ray source emits in particular no radiation.

By way of additionally irradiating the semiconductor material, free charge carriers can be generated herein, which can occupy the impurities in the semiconductor material and thus contribute to setting the equilibrium required for the operability. Heating increases the mobility of free charge carriers in the semiconductor material. Here the intended equilibrium is produced more easily and in particular more quickly and is also maintained in particular if the x-ray source emits no radiation onto the semiconductor material over a longer period of time and as result no free charge carriers are generated by the x-ray radiation.

Here the heating element comprises in particular an ohmic resistance, which is intended and set up for the controlled conversion of an electric current into heat. In this regard the light-emitting element preferably comprises a light source, which is set up to generate light in the visible range and/or in the UV range and/or in the IR range. Here the light-emitting element can have a number of LEDs.

The second power supply is favorably configured so that with a system reboot of the computed tomography device, the power supply of the second lot of components is interrupted. In particular, this means that the first voltage supply for providing the bias voltage for the semiconductor material during the system reboot is fed by the third power supply. In this way the heating element or the light-emitting element and with them, if applicable, existing regulation devices for regulating a temperature or an irradiation of the semiconductor material can also be rebooted.

The CT preferably comprises a first regulation device for regulating a temperature of the semiconductor material, wherein the first regulation device has a first non-volatile regulation element, which is intended and configured, with a separation of the first regulation device from an electrical power supply, to store an existing target value and/or an existing actual value of a temperature, and with a renewed electrical power supply of the first regulation device, to make available the stored target value or actual value in the first regulation device. Here the first regulation element preferably has a corresponding electronic module, which is configured for the non-volatile storage of the present target value and/or actual value of the temperature irrespective of an electrical power supply so that the electronic module provides the respectively stored value after a renewed connection to the electrical power supply. With a system reboot, the first regulation device therefore does not need to reregulate the temperature from scratch, instead the regulation can continue with the values which existed before the system reboot and the separation of the first regulation device from the electrical power supply which is associated therewith.

It has proven to be further advantageous if the CT has a second regulation device for regulating an irradiation of the semiconductor material, wherein the second regulation device has a second non-volatile storing regulation element, which is intended and set up, with a separation of the second regulation device from an electrical power supply, to store an existing target value and/or an existing actual value of an irradiation and with a renewed electrical power supply of the second regulation device, to make available the stored target value or actual value in the second regulation device. In this regard a target value or actual value of an irradiation can relate to an irradiation intensity or a physical radiation parameter which can be compared hereto and/or a frequency or a spectral parameter which can be compared hereto. A regulation of the irradiation can in particular also take place on the basis of the free charge carriers generated by the irradiation in the semiconductor material and determined accordingly as a sensor current.

To this end the second regulation element preferably has a corresponding electronic module, which is set up for the non-volatile storage of the existing target value and/or actual value of the irradiation irrespective of an electrical power supply so that the electronic module provides the respectively stored value after a renewed connection to the electrical power supply. With a system reboot, the second regulation device does therefore not need to reregulate the irradiation from scratch, instead the regulation can continue with the values which existed before the system reboot and the separation of the second regulation device from the electrical power supply which is associated therewith.

In a further advantageous embodiment, the CT comprises a second transmission path which can be separated from a first transmission path of the first power supply in terms of circuitry and is arranged at least partially on the ring mount, the second transmission path being interconnected with the second power supply. In this way the transmission paths for the first and the second power supply are realized in individual electric circuits which can be separated from one another so that the transmission paths do not need to be set up for different operating modes, but instead each of the two transmission paths is designed for the corresponding power supply and used accordingly. It is therefore possible to dispense with intelligent control elements for activating and deactivating individual components of the first or the second lot.

Here the second transmission path advantageously has a terminal, arranged on the ring mount, for a mains cable. Both the second transmission path and also its separation from the first transmission path can be realized particularly easily; for the second power supply the relevant mains cable is easily connected to the terminal.

The second lot of components is favorably arranged electrically insulated in the ring mount. In particular, the components of the second lot are arranged insulated on the ring mount so that the components of the first lot, which are not part of the second lot, in other words e.g. an x-ray source or cooling unit or fan, remain in a current- and voltage-free manner in the resting state, and can thus be maintained or replaced in the resting state. In this regard the second lot of components remains supplied with power via the second power supply. A maintenance or a replacement of the components only of the first lot can therefore be carried out so that the semiconductor material remains further operable and the CT is fully usable again immediately after terminating the maintenance or the replacement, in particular without further waiting times.

Expediently, for the method in the operating state, a temperature of the semiconductor material and/or an irradiation of the semiconductor material for maintaining the equilibrium are regulated with a first accuracy constant, wherein in an extended resting mode the temperature or the irradiation of the semiconductor material are regulated with a second accuracy constant which is greater than the first accuracy constant. The second accuracy constant is here and then below to be referred to as greater than the first accuracy constant, if a greater inaccuracy is tolerated by the second accuracy constant, and the regulation in the extended resting mode is thus "rougher" and in particular can take place with more potential deviation from an intended target value than in the operating state. A maximum deviation from a target value is preferably included as a first or second accuracy constant, wherein the maximum deviation from the target value determines when an intervention into the relevant control loop is actively performed by a correcting variable.

It has proven further advantageous for the method if, in the operating state, a temperature of the semiconductor material and/or an irradiation of the semiconductor material are regulated with a first accuracy constant in order to maintain the equilibrium and if in the process before a system reboot of the CT for the regulation in each case by a corresponding non-volatile-storing regulation element, a target value and/or an actual value of the temperature or the irradiation is stored and is made available for the regulation after the system reboot. In this regard, the regulation of the temperature of the irradiation can be immediately continued after the system reboot with high stability. Since the duration for a system reboot lies in the range of a few minutes, during the system reboot the semiconductor material can cool down to below the conditions to be assumed by only a few degrees, until the system reboot is completed, and the regulation can be continued. Here the irradiation can in particular be regulated on the basis of an instantaneously measured irradiation intensity or also on the basis of a measured current on free charge carriers. For this reason, continuation of the regulation in particular with the temperature values or the irradiation values, which existed before the system reboot, is advantageous.

Figure 1:
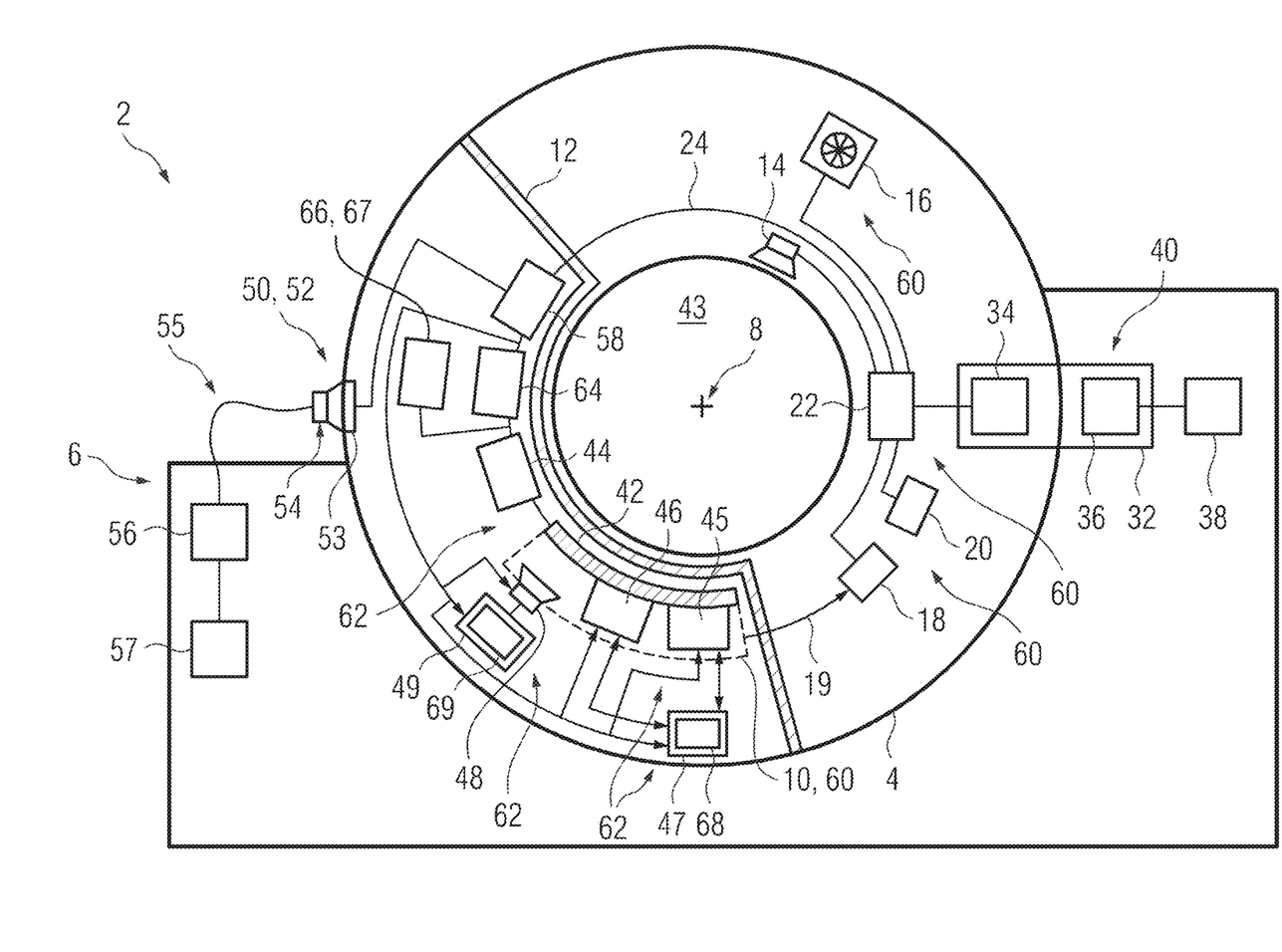
FIG. 1 a cross-sectional display of a CT with a second power supply for the x-ray detector arranged on the ring mount.

FIG. 1 shows a schematic representation of a cross-sectional display of a CT 2. Here the CT 2 comprises a ring mount 4 and a holding frame 6. Here the ring mount 4 is mounted rotatably with respect to the holding frame 6 about an axis 8 in the center of the ring mount 4 which is perpendicular to the image plane. The x-ray detector 10 is arranged in an electrical insulation 12 on the ring mount 4.

On the ring mount 4 an x-ray source 14, a fan 16, an image processor 18 and control electronics 20 are connected in a conducting manner to a central power distributor 22, from which a line 24 for supplying the x-ray detector 10 also discharges. The image processor 18 is connected to the x-ray detector 10 by way of an optical signal cable 19. A rotary anode with a drive, a cathode heater and a cooling unit are also arranged in the x-ray source 14 in a manner not shown in more detail. The central power distributor 22 is connected to a first transmission path 32, which has a component 34 which receives energy and which conducts the power to the central power distributor 22.

A component 36 of the first transmission path 32 which outputs energy and which is arranged on the holding frame 6 is connected to a first power source 38, which can be provided by a mains connection, for instance. The first power source 38, the first transmission path 32 and the central power distributor 22 together with the corresponding connection lines form the essential components of a first power supply 40. Here the component 34 receiving energy and the component 36 outputting energy can be embodied in each case as coils of a coil pair for an inductive energy transmission or as a collector ring with a collector ring contact.

The x-ray detector 10 has a layer of a semiconductor material 42, which is attached so that x-ray radiation (not shown in more detail) generated by the x-ray source 14 (and if applicable partially scattered and/or absorbed by an object positioned in the interior 43 of the ring mount 4) strikes the semiconductor material 42. In this regard the semiconductor material can be provided in particular by cadmium telluride or cadmium zinc telluride or also by a comparable semiconductor with similarly relevant properties.

The semiconductor material 42 is interconnected with a first voltage supply 44 so that a bias voltage can be applied to the semiconductor material 42 via the first voltage supply 44. Furthermore, the semiconductor material is thermally coupled to a heating element 45 and a cooling element 46. The heating element 45 is set up to heat the semiconductor material 42 in order to increase the mobility of free charge carriers there. In this way a saturation of the impurities in the semiconductor material 42 is facilitated on the one hand, on the other hand the linearity for free charge carriers is increased, which are generated by the x-ray radiation emitted by the x-ray source 14 in the semiconductor material 42. The cooling element 46 is set up to reduce the temperature of the semiconductor material 42, if this assumes a critical value as a result of an incident x-ray radiation.

The heating element 45 and the cooling element 46 are connected to a first regulation device 47, which is set up to regulate the temperature of the semiconductor material 42, and in this regard, in particular via heating, the mobility of free charge carriers is further enabled if the first power supply 40 is deactivated. For this purpose the first regulation device 47 is connected to a temperature sensor (not shown in more detail) which measures a temperature of the semiconductor material 42. A light-emitting element 48 is arranged on the ring mount in the immediate vicinity of the semiconductor material 42, and can be implemented e.g. by a number of LEDs and is set up to generate free charge carriers herein by irradiating the semiconductor material 42, the free charge carriers occupying the impurities thereof in particular by applying the bias voltage provided by the first voltage supply 44 to the semiconductor material 42. This results in further free charge carriers, which are generated by an x-ray radiation emitted by the x-ray source 14 and striking the semiconductor material 42, enabling a particularly linear behavior with respect to the detection of the x-ray radiation, since the impurities in an equilibrium which is produced as a result of the bias voltage are saturated, and the semiconductor material 42 is, as a result, fully operable.

The irradiation of the semiconductor material 42 is regulated here by way of a second regulation device 49, which for this purpose is connected to a light sensor which is not shown in more detail and is arranged in the immediate vicinity of the semiconductor material 42, the light sensor measuring an irradiation intensity and thus permitting conclusions to be drawn as to an irradiation intensity on the semiconductor material 42.

The first power supply 40 is connected via the central power distributor 22 to the x-ray source 14, the fan 16, the control electronics 20 and the image processor 18, and via the line 24 and a protective switch 58 connected hereto to the first voltage supply 44, the heating element 45, the cooling element 46, the first regulation device 47, the light-emitting element 48 and the second regulation device 49. In the operating state of the CT 2, the components interconnected with the protective switch 58 obtain their electrical power supply by way of the line 24 through the first power supply 40; the protective circuit 58 is enabled here in a corresponding switching state so that a power flow is enabled toward the components.

The components connected to the first power supply 40 directly on the central power distributor 22 (in other words not via the protective circuit 58) only obtain a power in the operating state. If the first power supply 40 is interrupted, because the CT is to be transferred overnight into a resting mode, or a system reboot is to take place, an electrical power supply does not take place for any of the components connected directly to the central power distributor 22.

For the resting mode, in which the first power supply 40 is deactivated, the CT 2 has a second power supply 50 which is connected to the protective switch 58. The protective switch 58 ensures that in the event that the first power supply 40 is deactivated, and an electrical power supply takes place by way of the second power supply 50, there is no backflow of power to the central power distributor 22 and thus in particular the x-ray source 14, the fan 16, the control electronics 20 and the image processor 18 remain current- and voltage-free and can thus be maintained or replaced in the resting state. For this purpose the insulation 12 is additionally intended for the components interconnected with the protective switch 58.

The second power supply 50 has a second transmission path 52 with a component 53 which receives energy and is arranged on the ring mount 4 and a component 54 which outputs energy and is arranged at least partially on the holding frame 6. The component 53 which receives energy is currently formed by a terminal for a mains plug. The component 54 which outputs energy comprises the mains plug and a mains cable 55, which is interconnected with the holding frame 6 with a UPS 56, which is connected for its part with a mains terminal 57 for connection to a mains supply, not shown in more detail. The UPS 56 is set up to maintain the second power supply 50 in the case of a power failure. Indeed hospitals often have a separate UPS, but CTs are also increasingly used in doctor's practices or smaller treatment centers without separate UPS so that the UPS 56 here guarantees the operation of the second power supply 50.

The component 53 which receives energy and the component 54 of the second transmission path 52 which outputs energy can however, alternatively to the embodiment shown, or also additionally hereto, comprise a pair of induction coils for an inductive energy transmission.

In the resting state, in the semiconductor material 42 of the x-ray detector 10, a temperature set by the heating element 45 or the cooling element 46 is also maintained by way of the bias voltage of the first voltage supply 44 and the equilibrium of the states of occupation of the impurities is maintained by way of an irradiation effected by the light-emitting element 48, wherein the power is now supplied by way of the second power supply 50.

On account of the electric insulation 12 and the protective circuit 58, the ring mount, as far as the x-ray detector 10 itself, is voltage-free in the resting state, so that in this time maintenance or repair work, which does not relate to the x-ray detector 10, can be carried out.

The loads arranged on the ring mount for the image generation thus form a first lot 60 of components, which, in the operating state of the CT 2, are supplied with power by the first power supply 40. As a result of the insulation 12 and the separation from the central power distributor 22 in terms of circuitry via the protective circuit 58, the first voltage supply 44, the heating element 45, the cooling element 46, the first regulation device 47, the light-emitting element 48 and the second regulation device 49 form a second lot 62 of components, which, in the resting state, in other words when the first power supply 40 is switched off, are supplied with power by the second power supply 50, in order to keep the semiconductor material 42 of the x-ray detector 10 in an operable state as far as possible.

Also in the operating state, here the semiconductor material 42 of the x-ray detector 10 is kept operable by the components of the second lot 62, wherein if applicable during an individual x-ray recording, the light-emitting element 48 and if applicable the heating element 45 can be deactivated. In the operating state, in this regard the components of the second lot 62 can obtain their power via the first power supply 40, so that the second power supply 50 only assumes the electrical power supply of the second lot 62 of components in the resting state.

A voltage buffer 64 is connected between the first voltage supply 44 and the protective switch 58 (and thus also the second power supply 50), and compensates for voltage fluctuations occurring with a use of the UPS 56 in order to keep the bias voltage as constant as possible with a power failure and the use of the UPS 56 which results therefrom.

If a system reboot is now to be carried out, the second power supply 50 is also interrupted in a controlled manner for the reboot. In order still to be able to maintain the bias voltage, a battery 67 with the first voltage supply 44 is switchably connected in a manner not shown as a third power supply 66. The third power supply 66 provides the necessary power during the system start, in order furthermore to be able to apply the bias voltage to the semiconductor material 42. Since the system reboot lasts at most just a few minutes, failure of the heating element 45 and the light-emitting element 48 here can be negligible as a result of the comparably slow temperature relaxation or the instantaneous irradiation by the light element 48 after the system reboot.

In order in the process to be able to continue the temperature regulation and the regulation of the irradiation after the system reboot as closely as possible to the last values, the first regulation device 47 has a first non-volatile-storing regulation element 68, which stores the actual value existing before the system start and/or target value of the temperature even when the second power supply 50 is interrupted and thus stores the electrical power supply of the first regulation device 47. The regulation of the temperature can then be continued for instance with the last known actual value as a starting value.

Similarly, the second regulation device 49 has a second non-volatile-storing regulation element 69, which stores the actual value and/or target value of an irradiation intensity existing before the system start and if applicable frequency or wavelength even when the second power supply 50 is interrupted, and thus stores the electrical power supply of the second regulation device 49. The regulation can then likewise be continued with the last known actual value as a starting value.

In particular, here the regulation can take place via the first regulation device 47 and the second regulation device 49 in the resting state to a less "rough" degree (i.e. that e.g. a marginally greater deviation from the respective target value is tolerated) than in the operating state. A type of extended resting mode is defined in this way. This can reduce the energy consumption, wherein the semiconductor material 42 is still kept almost ideally operable.

Although the invention has been illustrated and described in more detail by the preferred example embodiment, the invention is not restricted by this example embodiment. Other variations can be derived herefrom by the person skilled in the art without departing from the scope of protection of the invention.

Although the invention has been illustrated and described in greater detail with reference to the referred example embodiments, the invention is not restricted thereby. Other variations and combinations can be derived herefrom by the person skilled in the art without departing from the essential concept of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computed tomography device comprising:
   a holding frame; and
   a ring mount, the ring mount being movably mounted to the holding frame, and the ring mount including an x-ray detector, with a semiconductor material, operable in an equilibrium of statistical states of occupation;
   a first power supply, set up to supply power, in an operating state of the computed tomography device, to a first lot of components of the computed tomography device, the first lot of components being arranged on the ring mount for an image generation process;
   a second power supply, separable from the first power supply in terms of circuitry, to supply power to a second lot of components of the computed tomography device in a resting state of the computed tomography device, the components of the second lot being set up to hold the semiconductor material in the equilibrium, the second lot of components including a first voltage supply for applying a bias voltage to the semiconductor material;
   an uninterruptible power supply, interconnectable with the second lot of components; and
   a third power supply, separable from the first power supply and the second power supply in terms of circuitry, the third power supply being set up, with a system reboot of the computed tomography device, to supply power to the first voltage supply to maintain the bias voltage on the semiconductor material during the system reboot.

2. The computed tomography device of claim 1, wherein the second lot of components includes at least one of a heating element to heat the semiconductor material and a light-emitting element to irradiate the semiconductor material.

3. The computed tomography device of claim 2, wherein the second power supply is configured so that, with a system reboot of the computed tomography device, the power supply of the second lot of components is interrupted.

4. The computed tomography device of claim 3, further comprising:
   a first regulation device to regulate a temperature of the semiconductor material, the first regulation device including a first non-volatile-storing regulation element, set up, with a separation of the first regulation device from an electrical power supply, to store at least one of an existing target value of a temperature and an existing actual value of the temperature and with a renewed power supply of the first regulation device, to make the at least one of the stored target value and the stored actual value available in the first regulation device.

5. The computed tomography device of claim 3, further comprising:
   a second regulation device to regulate an irradiation of the semiconductor material, the second regulation device including a second non-volatile-storing regulation element, set up, with a separation of the second regulation device from an electrical power supply, to store at least one of an existing target value of an irradiation and an existing actual value of an irradiation and with a renewed electrical power supply of the second regulation device, to make the at least one of the stored target value and actual value available in the second regulation device.

6. The computed tomography device of claim 2, further comprising:
   a first regulation device to regulate a temperature of the semiconductor material, the first regulation device including a first non-volatile-storing regulation element, set up, with a separation of the first regulation device from an electrical power supply, to store at least one of an existing target value of a temperature and an existing actual value of the temperature and with a renewed power supply of the first regulation device, to make the at least one of the stored target value and the stored actual value available in the first regulation device.

7. The computed tomography device of claim 2, further comprising:
   a second regulation device to regulate an irradiation of the semiconductor material, the second regulation device including a second non-volatile-storing regulation element, set up, with a separation of the second regulation device from an electrical power supply, to store at least one of an existing target value of an irradiation and an existing actual value of an irradiation and with a renewed electrical power supply of the second regulation device, to make the at least one of the stored target value and actual value available in the second regulation device.

8. The computed tomography device of claim 1, further comprising:
   a second transmission path, separable from a first transmission path of the first power supply in terms of circuitry, arranged at least partially on the ring mount and interconnected with the second power supply.

9. The computed tomography device of claim 8, wherein the second transmission path includes a terminal for a mains cable arranged on the ring mount.

10. The computed tomography device of claim 1, wherein the second lot of components in the ring mount are arranged in an electrically isolated manner.

11. The computed tomography device of claim 1, further comprising:
    a voltage buffer, connected between the uninterruptible power supply and the first voltage supply, to compensate for a voltage fluctuation with a use of the uninterruptible power supply.

12. A method for operating a computed tomography device including a holding frame and a ring mount, the ring mount being movably mounted with respect to the holding frame, the ring mount including an x-ray detector with a semiconductor material, operable in an equilibrium of statistical states of occupation, the method comprising:

supplying, in an operating state of the computed tomography device, a first lot of components arranged on the ring mount with power via a first power supply and carrying out a medical imaging process via components of the first lot; and supplying, in a resting state of the computed tomography device, a second lot of components arranged on the ring mount with power via a second power supply, the second power supply being separated from the first power supply in terms of circuitry and holding the semiconductor material in the equilibrium via the components of the second lot, the second lot of components including a first voltage supply for applying a bias voltage to the semiconductor material, and an uninterruptible power supply being interconnectable with the second lot of components; and supplying, during a system reboot of the computed tomography device, power to the first voltage supply via a third power supply to maintain the bias voltage of the semiconductor material, the third power supply being separable from the first power supply and the second power supply in terms of circuitry.

13. The method of claim 12, wherein in the operating state, at least one of a temperature of the semiconductor material and an irradiation of the semiconductor material is regulated in order to maintain the equilibrium with a first accuracy constant, and wherein, in an extended resting mode, at least one of the temperature of the semiconductor material and the irradiation of the semiconductor material are regulated with a second accuracy constant, the second accuracy constant being relatively greater than the first accuracy constant.

14. The method of claim 12, wherein in the operating state, at least one of a temperature of the semiconductor material and an irradiation of the semiconductor material is regulated in order to maintain the equilibrium with a first accuracy constant, and wherein, before the system reboot of the computed tomography device for the regulation, at least one of a target value of at least one of the temperature and irradiation and an actual value of at least one of the temperature and the irradiation is stored via a corresponding non-volatile-storing regulation element, and made available for the regulation after the system reboot.

* * * * *